United States Patent
Hoult et al.

(10) Patent No.: US 7,595,884 B2
(45) Date of Patent: Sep. 29, 2009

(54) MEASUREMENT OF SAMPLE REFLECTANCE

(75) Inventors: Robert Alan Hoult, Buckinghamshire (GB); Paul Alexander Evetts, Twyford (GB)

(73) Assignee: PerkinElmer LAS, Inc., Boston, MA (US)

( * ) Notice: Subject to any disclaimer, the term of this patent is extended or adjusted under 35 U.S.C. 154(b) by 353 days.

(21) Appl. No.: 11/040,535

(22) Filed: Jan. 21, 2005

(65) Prior Publication Data
US 2005/0185185 A1  Aug. 25, 2005

(30) Foreign Application Priority Data
Jan. 20, 2004  (EP)  ................... 04250256

(51) Int. Cl.
*G01N 21/01* (2006.01)
(52) U.S. Cl. ..................................... 356/445
(58) Field of Classification Search ................. 356/445
See application file for complete search history.

(56) References Cited

U.S. PATENT DOCUMENTS

| 4,657,390 A | * | 4/1987 | Doyle ......................... 356/451 |
| 4,712,912 A | * | 12/1987 | Messerschmidt ............. 356/73 |
| 5,048,970 A | * | 9/1991 | Milosevic et al. ........... 356/445 |
| 5,088,821 A | * | 2/1992 | Milosevic ..................... 356/319 |
| 5,106,196 A | | 4/1992 | Brierley ....................... 356/445 |
| 5,262,845 A | * | 11/1993 | Milosevic et al. ........... 356/445 |
| 5,903,351 A | | 5/1999 | Jeong et al. |
| 6,184,980 B1 | * | 2/2001 | Brown et al. ................. 356/300 |
| 6,310,348 B1 | | 10/2001 | Melling et al. .............. 250/341 |
| 7,265,844 B2 | * | 9/2007 | Codner et al. ................ 356/445 |
| 2004/0136005 A1 | * | 7/2004 | Hammer et al. ............. 356/445 |

FOREIGN PATENT DOCUMENTS

| EP | 0713 082 A2 | 5/1996 |
| WO | WO 02/084237 A1 | 10/2002 |
| WO | WO02082062 A1 * | 10/2002 |

OTHER PUBLICATIONS

European Search Report—Jan. 24, 2005.
Extended European Search Report; EP 08 07 5194; Mar. 24, 2009; 8 pages.
Extended European Search Report; EP 08 07 5195; Mar. 23, 2009; 8 pages.
Extended European Search Report; EP 08 07 5196; Mar. 24, 2009; 9 pages.

* cited by examiner

*Primary Examiner*—Tarifur Chowdhury
*Assistant Examiner*—Tara S Pajoohi
(74) *Attorney, Agent, or Firm*—St. Onge Steward Johnston & Reens LLC

(57) ABSTRACT

An accessory for a spectrometer for carrying out measurements of specular reflectance of a sample. The accessory is designed so that all components can be located in a housing and the sample can be located horizontally on a top-plate of the housing with the components disposed below the plane of that plate.

4 Claims, 17 Drawing Sheets

MEASUREMENT OF SAMPLE REFLECTANCE

This application claims priority from pending European application no. 04250265.8 filed Jan. 20, 2004.

FIELD OF THE INVENTION

This invention relates to spectrometry and in particular relates to an assembly of components which can be used with a spectrometer in order to measure specular reflectance of a sample.

Spectrometers are used to analyse samples to identify their properties. A spectrometer usually includes a source of radiation which is used to irradiate a sample and a receiver for receiving radiation either reflected from or transmitted by the sample. The receiver signal is analysed to produce a spectrum which then provides information relating to the sample.

There is a need in spectrometry to make accurate measurements of specular reflectance of a sample over a substantial range of angles and over a wide range of wavelengths, which typically can extend from the ultraviolet (UV) through to the near infrared (NIR). There is an absence of suitable reflectance standards which means that the reflectance of samples has to be measured directly without reference to a standard reflector. Currently there is a lack of suitable equipment available at a reasonable price that can measure reflectance over a significant range of angles and is sufficiently small and compact to be incorporated into modern spectrometers.

Reflectance measurements are usually made using accessories which can be removably coupled to a spectrometer. One known accessory design operates on the basic principle of providing two alternative paths for the light beam in the instrument sample compartment. One path is a sample path in which the beam reflects off the sample and is returned to the spectrometer detector. The other path is a background path in which the beam is directed to the detector and does not reflect off the sample. The ratio of the detected signals is a measure of the sample reflectivity, but its accuracy is dependent upon whether there are differences in the beam transmission energy on the two paths ignoring the effect of the sample itself. Since optical components do not reflect or transmit perfectly, great care is needed to match the performance of the components in the two configurations and the optical path is arranged so that switch-over between paths can be made by reversing two mirrors so that in each configuration the beam is reflected at an identical angle albeit reversed because of the presence or absence of the reflecting sample.

Also known accessories usually make use of the detector of the instrument with which they are used and this can lead to difficulties in providing an arrangement of optical components which will permit reflectance measurements over a wide range of angle of incidence of the beam on the sample.

Another known problem is that of beam and/or detector inhomogeneity. If both are non-uniform the output of the detector changes when the mirror angles are reversed and some form of beam homogenisation is required.

The present invention is concerned with an assembly of components which can be provided as a spectrometer accessory and which is designed to alleviate the problems referred to.

According to one aspect of the present invention there is provided an assembly of components for use with a spectrometer to enable reflectance measurements to be made on a sample, said assembly comprising a sample location, optical elements for directing analysing radiation to said sample location and a detector for receiving radiation reflected from the sample, at least one of the optical elements including a mirror which is rotatable and translatable to enable radiation to be incident on the sample over a range of angles. The sample location may be arranged so that in use the sample is generally horizontal to facilitate sample placement. The optical elements may include a path length compensator. The path length compensator may comprise a mirror which can move linearly and that mirror may comprise a roof mirror.

The detector may be mounted so as to be pivotable relative to the sample. The detector may also be mounted so that it can move linearly relative to the sample. The detector may form part of the detector sub-assembly which includes two detector elements responsive to different wavelengths of radiation. One of the detector elements may have associated therewith an optical scrambler for scrambling the radiation prior to it being incident on the detector element. The scrambler may be a light pipe.

The sample location may be fixed.

The optical elements may be located in a housing and the assembly can take the form of an accessory for a spectrometer. The sample location may be located on the upper surface of the housing. The housing may have an aperture in its upper wall through which the radiation can pass to the sample location.

Another aspect of the invention provides an accessory for use with a spectrometer to enable reflectance measurements to be made on a sample, said accessory comprising a housing providing a sample location, optical elements disposed in said housing for directing analysing radiation to said sample location and a detector for receiving radiation reflected from the sample, wherein the sample location is provided on an upper surface of the housing. The upper wall of the housing may include an aperture through which the radiation can pass to the sample location. The upper wall may include a shutter for opening and closing the aperture.

The accessory may be locatable in the spectrometer in a position normally occupied by the detector of the spectrometer when it is operating without the accessory.

A further aspect of the invention provides an assembly of components for use with a spectrometer to enable reflectance measurements to be made on a sample comprising a sample location, optical elements for directing analysing radiation to said sample location and a detector for receiving radiation reflected from said sample, wherein an optical scrambler in the form of a light pipe is associated with the detector, said radiation passing through the light pipe prior to the detector in order to minimise the effect of inhomogeneities in the detector.

A further aspect of the invention provides an assembly of components for use with a spectrometer to enable reflectance measurements to be made on the sample, said assembly comprising a sample location, a first reflector for receiving analysing radiation propagating generally horizontally and for reflecting the radiation at least partially upwardly to a second reflector, a third reflector for receiving radiation from the second reflector and for directing the radiation along a generally horizontal path which is horizontally displaced relative to that of the incoming radiation, a fourth reflector for directing the radiation towards the sample location and a detector for receiving radiation reflected from the sample. The direction of radiation propagating from the third reflector may be generally opposite to that of the incoming radiation. The third reflector may be a roof mirror. The third reflector can be movable linearly so that it can act as a path length compensator.

The invention will be described now by way of example only, with particular reference to the accompanying drawings.

DETAILED DESCRIPTION OF THE DRAWINGS

Figure 1:
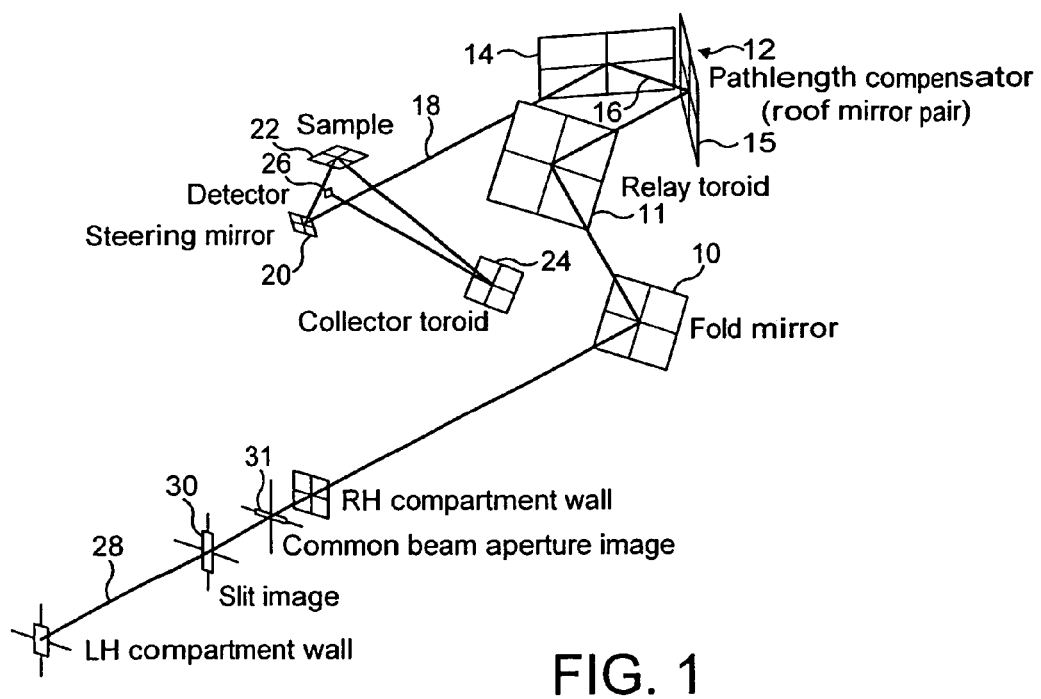
FIG. 1 is a schematic view of a reflectance accessory in accordance with an embodiment of the present invention.

FIG. 1 of the drawings shows schematically an embodiment of an accessory which can be used to carry out reflectance measurements on a sample. The accessory comprises a first mirror (10) which acts as a fold mirror and the angle of inclination of this mirror is adjustable. A second mirror which is a relay toroid (11) is mounted diagonally upwardly from the mirror (10) so that it can receive radiation reflected from the fold mirror (10). The inclination of the mirror (11) is also adjustable. Radiation reflected from the mirror (11) is directed horizontally towards a path length compensator (12). The path length compensator (12) takes the form of a 90° roof mirror pair having mirror elements (14 and 15). The mirror elements (14 and 15) are mounted so that the plane of each mirror lies substantially vertically whereby incoming radiation propagating horizontally from the mirror (11) is reflected from the mirror (15) along a horizontal path (16) towards the mirror (14) from which it is reflected along a further horizontal path (18).

The beam (18) reflected from the mirror (14) is incident on a steering mirror (20). The steering mirror (20) is mounted so that its angle of inclination can be adjusted and also its linear position along the path of the beam (18) can also be adjusted. As shown in FIG. 1 radiation striking the steering mirror (20) is directed diagonally upwardly towards a sample location (22). A collector toroid mirror (24) is mounted downwardly from the sample location (22) so that it can receive radiation reflected from a sample at the sample location (22) and reflect it towards a detector assembly (26). The steering mirror (20) can be pivoted to a position in which it reflects the beam (18) towards the collector mirror (24) without being incident on the sample.

As will be appreciated from the description to follow the assembly of components shown in FIG. 1 are constructed as an accessory for a spectrometer. When mounted in the spectrometer the accessory can receive a beam of radiation (28) produced from the radiation source of the spectrometer. The incoming beam is rectangular in cross-section and passes through an image of the spectrometer slit controlling the width of the beam (30) and a common beam aperture image controlling the height of the beam (31) before propagating to the fold mirror (10). The arrangement is such that the slits and the common beam aperture are imaged on to a sample at about unity magnification. The beam is first folded diagonally upwardly by the mirror (10) towards the relay toroid mirror (11). The purpose of relay toroid (11) is to refocus the image onto the sample. The relay toroid redirects the beam horizontally towards mirrors (14 and 15). The pair of mirrors (14, 15) can be moved horizontally parallel to the incoming beams to provide beam pathlength compensation. The roof mirror also shifts the beam laterally in a horizontal plane. The beam (18) from the path length compensator becomes the input beam for the steering mirror (20) which directs the beam towards the sample location (22). The beam is reflected towards the collector toroid and then to the detector assembly (26). The collector toroid is provided to refocus the beam. Also the collector toroid is mounted so that the beam is reflected up to around 30° out of a vertical plane to allow suitable location of the detector assembly. Signals produced by a detector of the detector assembly (26) can then be processed to measure the reflectance.

In order to enable reflectance measurements to be made over a range of angles, the steering mirror is adjustable both in position and inclination so that the angle of incidence of the beam propagating from the steering mirror to the sample location can be changed. As the angle of incidence changes the angle of reflection from the sample also changes and in order to allow for this it will be seen that the detector assembly (26) is mounted so that it can be moved both pivotally and linearly in order to receive radiation transmitted from the sample. Also the mirror (14 and 15) can be moved linearly in order to provide path length compensation which is required as a result of movement of the other elements.

Figure 1A:
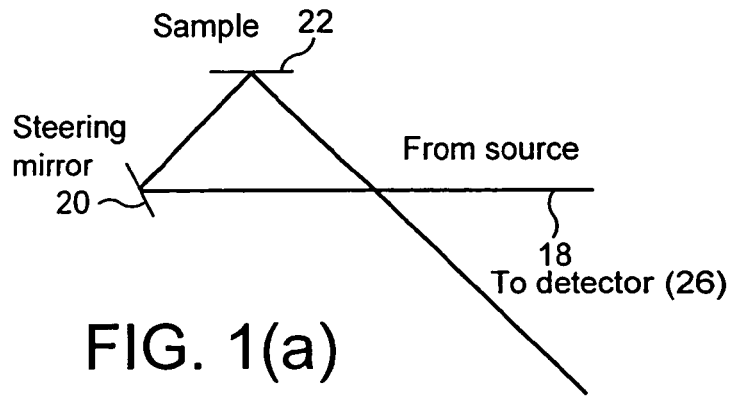
FIGS. 1(a) to 1(d) are schematic views illustrating the operation of the accessory of FIG. 1.
Figure 1B:
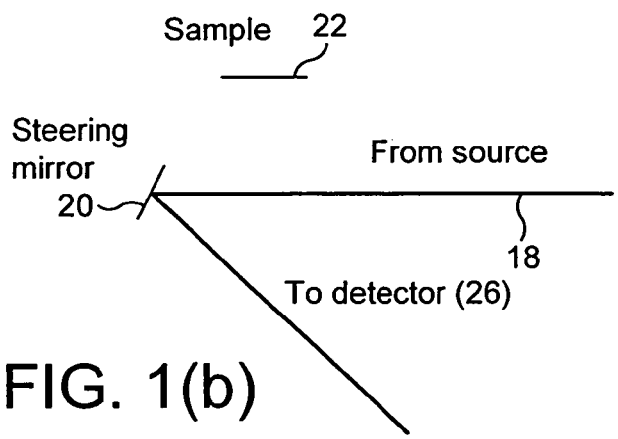

FIGS. 1(a) to 1(d) illustrate schematically the optical principles of the accessory. FIG. 1(a) shows the beam (18) reflected by the steering mirror (20) on to the sample at an angle of incidence of 45°. The beam propagates from the sample to detector. FIG. 1(b) shows the configuration for the background measurement. In this configuration the steering mirror (20) has been pivoted to the complementary angle so that the beam is directed to the detector without being reflected from the sample. In this configuration the detector assembly is moved vertically downwards and it can be shown that the vertical distance that it has to be moved is twice the vertical separation of the sample plane and the beam (18).

To a good approximation the same area of the steering mirror is illuminated at the same (complementary) angle in both configurations. Also the same region of the detector is illuminated and the pathlengths are identical. The image on the detector is, however, inverted between the two configurations which, given a typical non-uniform light beam, means that for accurate measurements either the detector has to be very uniform or an optical scrambler is required.

Figure 1C:
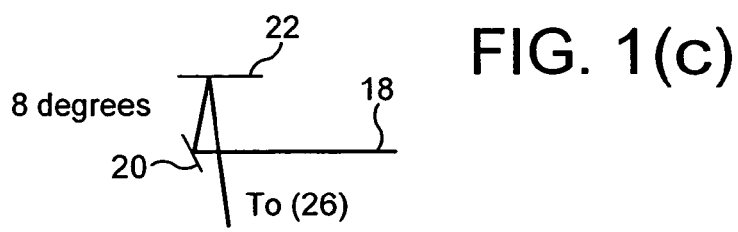
Figure 1D:
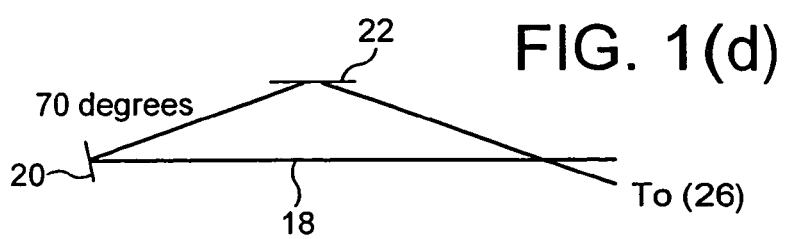
Figure 2:
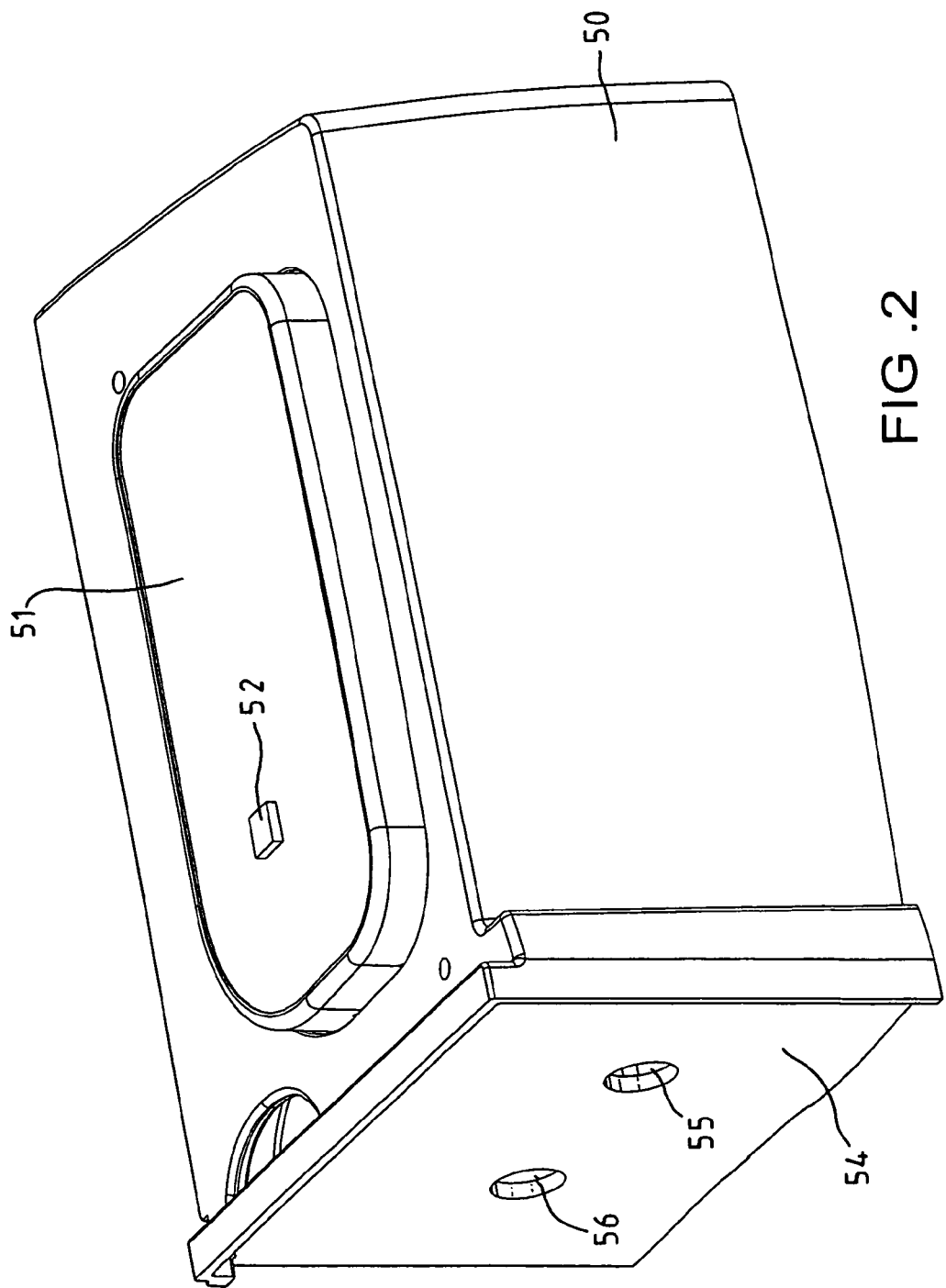
FIG. 2 is a perspective view from the front left of a reflectance accessory in accordance with an embodiment of the present invention.

FIGS. 1(c) and 1(d) illustrate schematically the sample configurations at the opposite ends of the range of possible angles incidence. FIG. 1(c) shows an angle of incidence of 8° and FIG. 1(d) shows an angle of incidence of 70°. These views show the need for the steering mirror (20) to translate as well as rotate. The detector also needs to rotate on an arc centred on the sample spot and also to move vertically downwards for the background measurement. The drawings also illustrate that the components of the accessory require careful location to avoid beam interruptions.

FIGS. 2 to 12 illustrate a specific embodiment of a spectrometer accessory operating on the principles shown generally in FIG. 1. This accessory has been designed for use with a PerkinElmer Lambda 950 spectrometer and is locatable in the compartment normally occupied by the detector of such an instrument. The accessory comprises a housing or cover (50) which has a top plate (51) which provides a sample location (52) at which a sample can be placed horizontally. The top plate can have covering layer of soft plastic material such as Teflon or Mylar to avoid possible damage to the optical surface of the sample. At the sample location (52) there is an aperture in the top plate (51) which can be closed by a shutter which is slidable between an open and a closed position. One side wall (54) of the housing (50) has an opening (55) through which the beam (28) shown in FIG. 1 can propagate. There is also a second aperture (56) through which the reference beam of the spectrometer can propagate.

FIGS. 3 to 10 illustrate the components which are accommodated within the housing (50). The fold mirror is shown at (10) and is mounted on an adjustable bracket (58). The toroid mirror (11) is mounted diagonally upwardly from the fold mirror (10) and is suspended from the underside of the top plate on a second adjustable bracket spaced horizontally from the path length compensator (12). The mirrors (14 and 15) of the path length compensator are mounted upon a casting (60) (see FIG. 5) and this casting is linked to an assembly comprising a lead screw (61) which is drivable by a motor (62) through gears (64) so that when the motor (62) is energised the lead screw (61) rotates and causes linear movement of the pair of mirrors (14 and 15) along a path guided by slides (65 and 66). This linear movement is parallel to the path of the beam (18) shown in FIG. 1.

Figure 3:
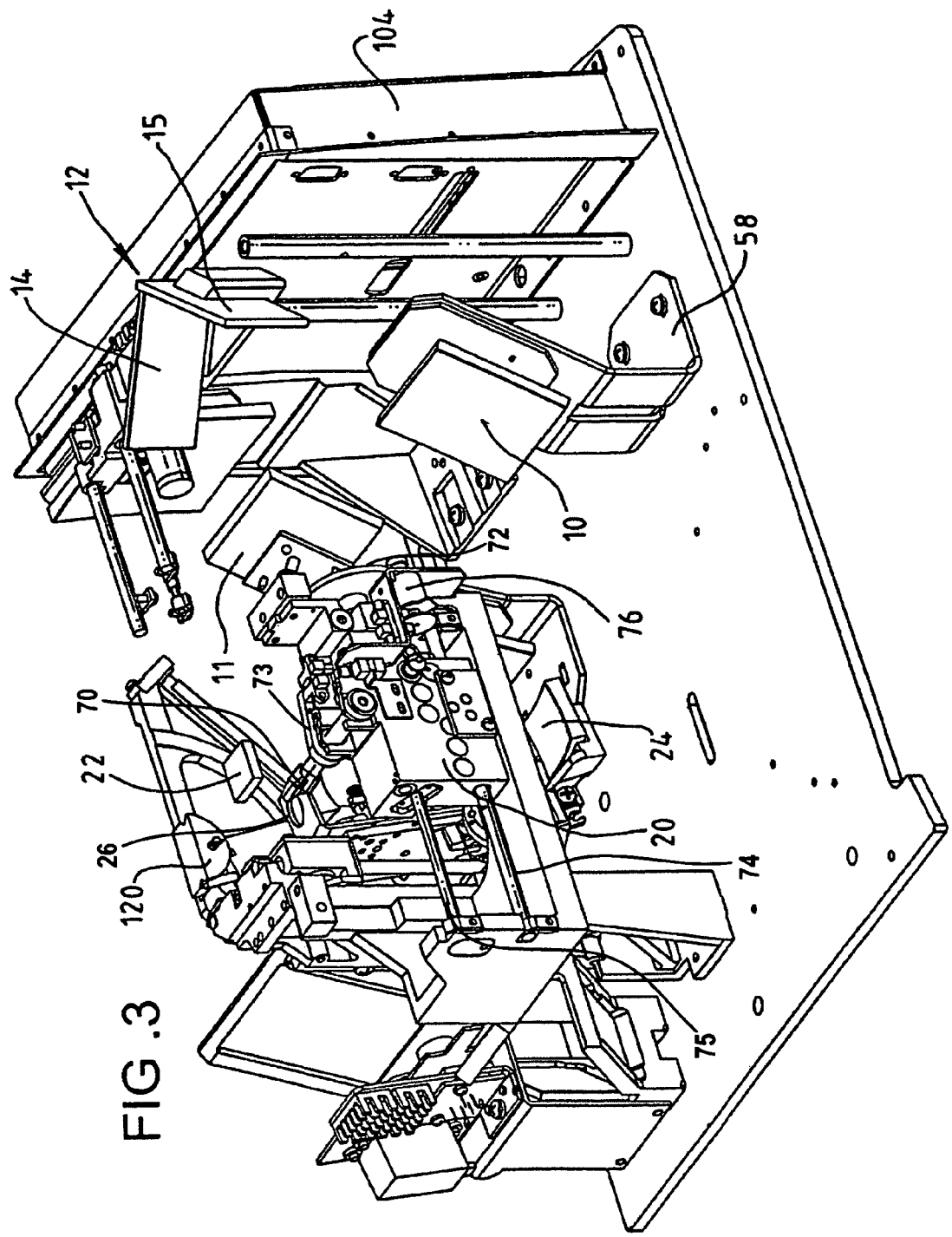
FIG. 3 is a perspective view from the front left of the accessory of FIG. 2 with the cover removed.
Figure 4:
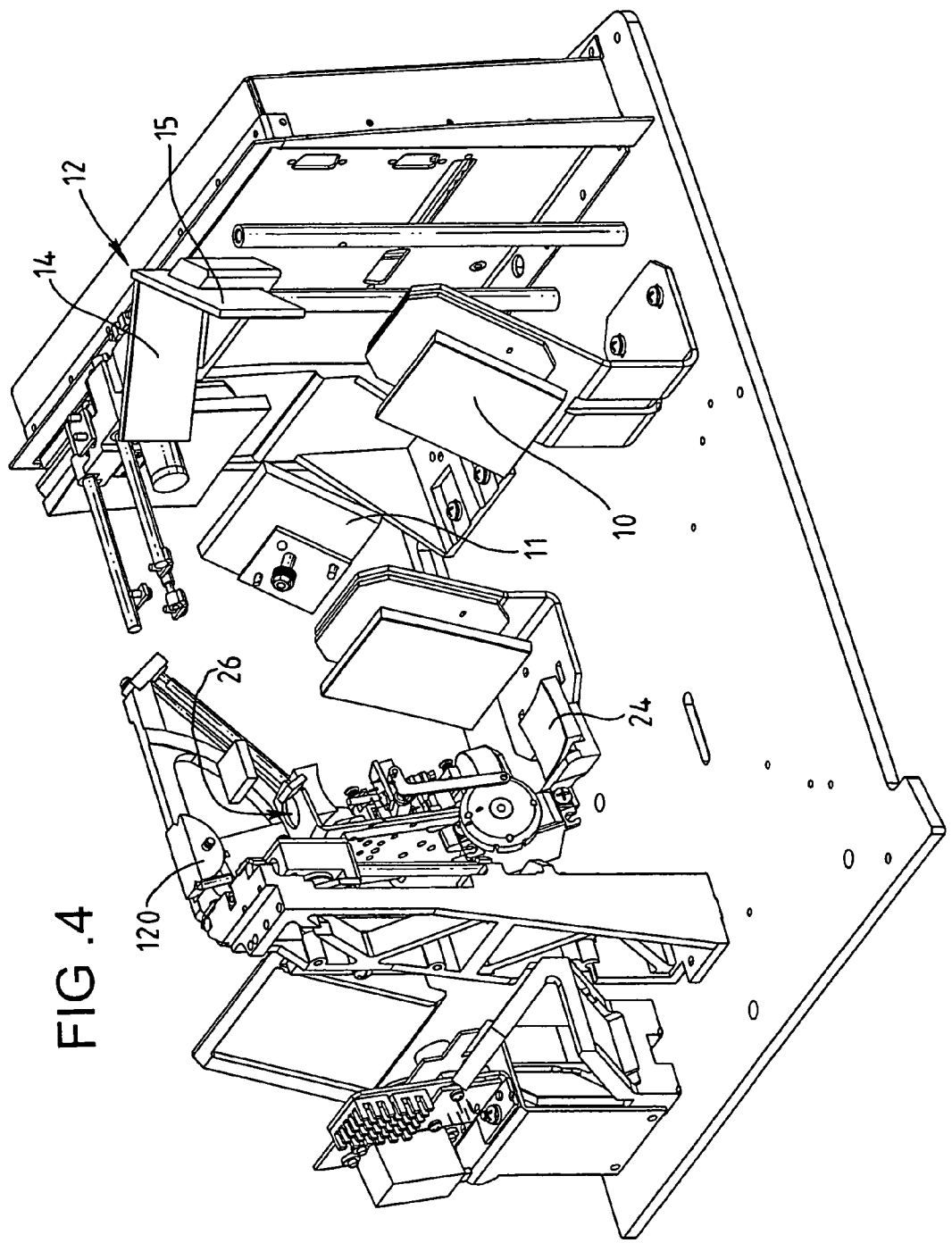
FIG. 4 is a perspective view similar to FIG. 3, but with the steering mirror assembly removed.
Figure 5:
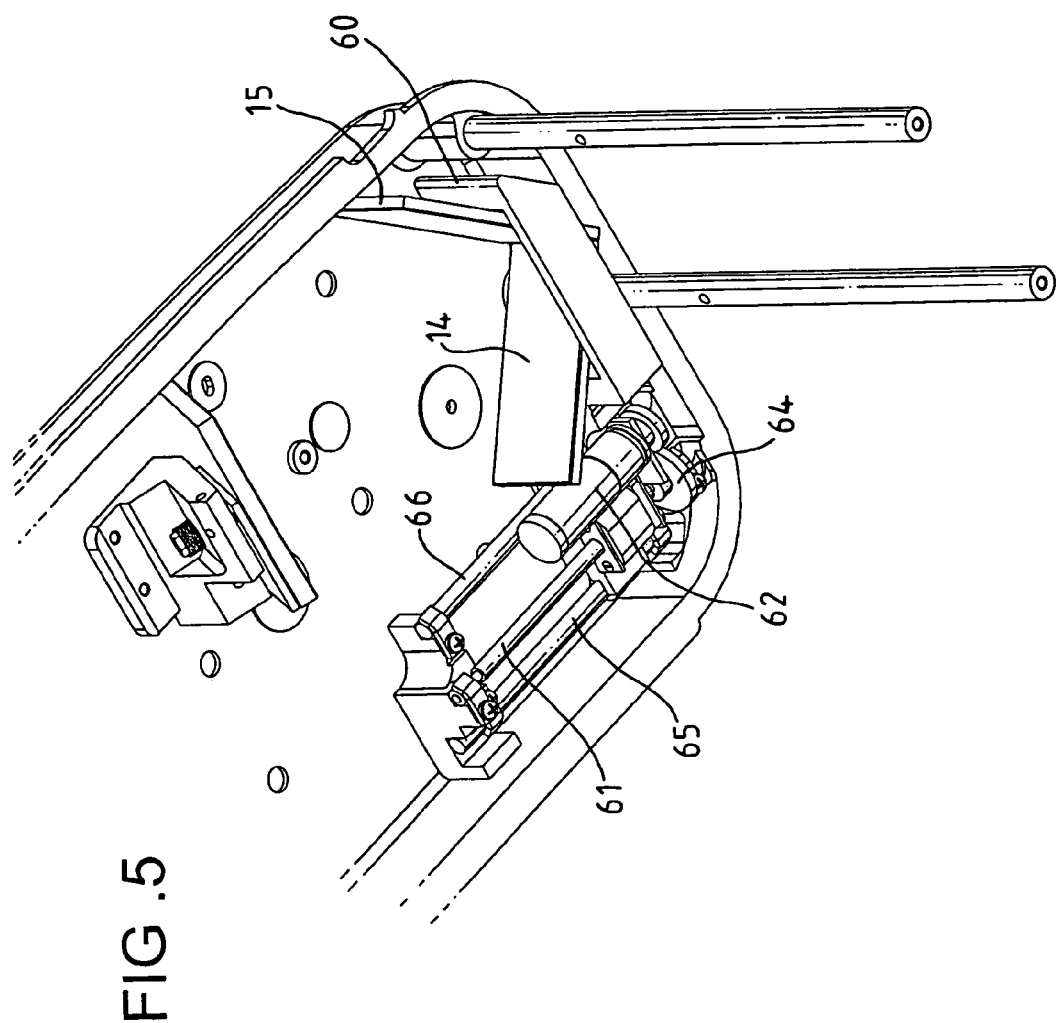
FIG. 5 is a view from below of the pathlength compensator.
Figure 6:
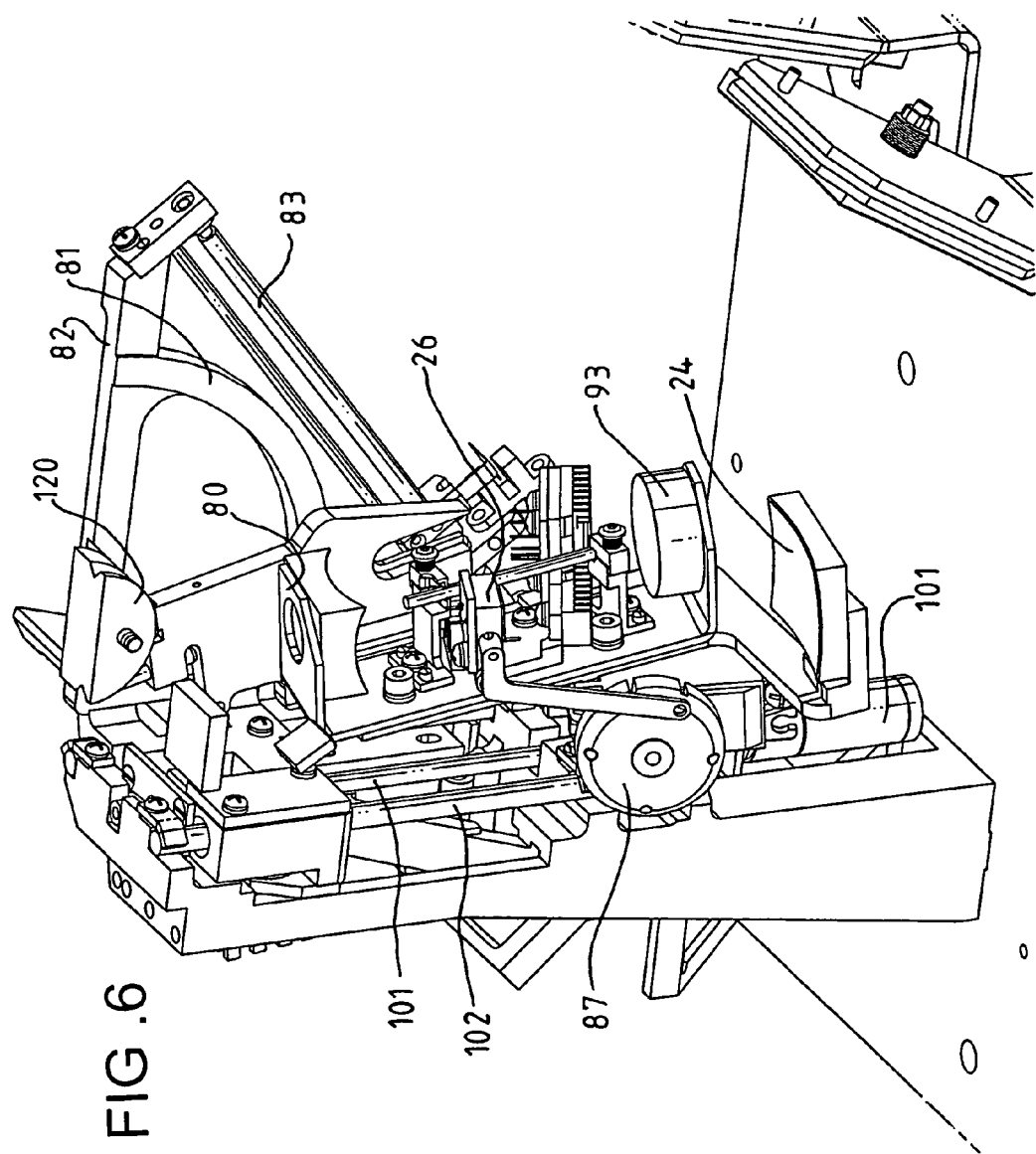
FIG. 6 is a perspective view from the front right of the detector assembly.
Figure 7:
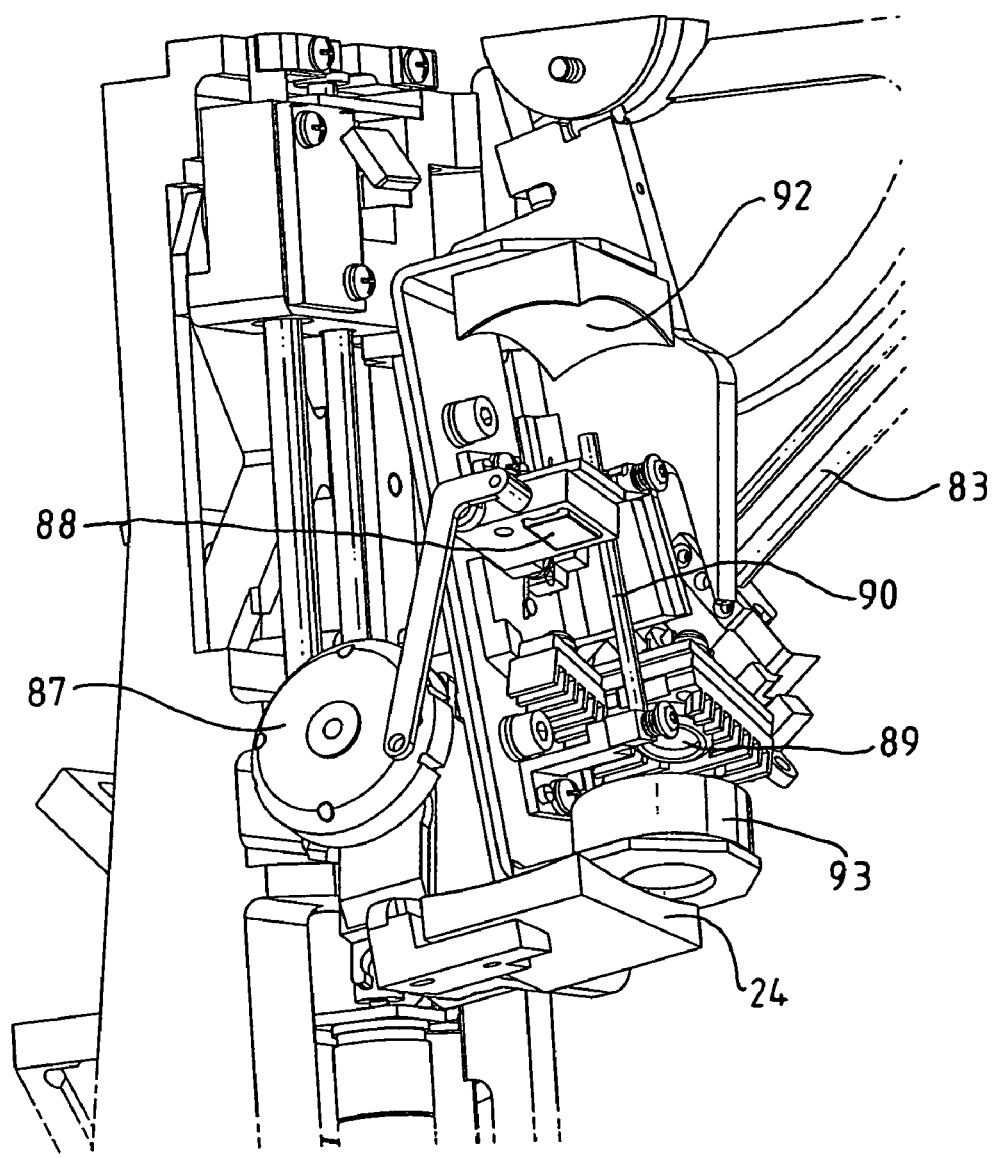
FIG. 7 is a more detailed view of the detector assembly.
Figure 8:
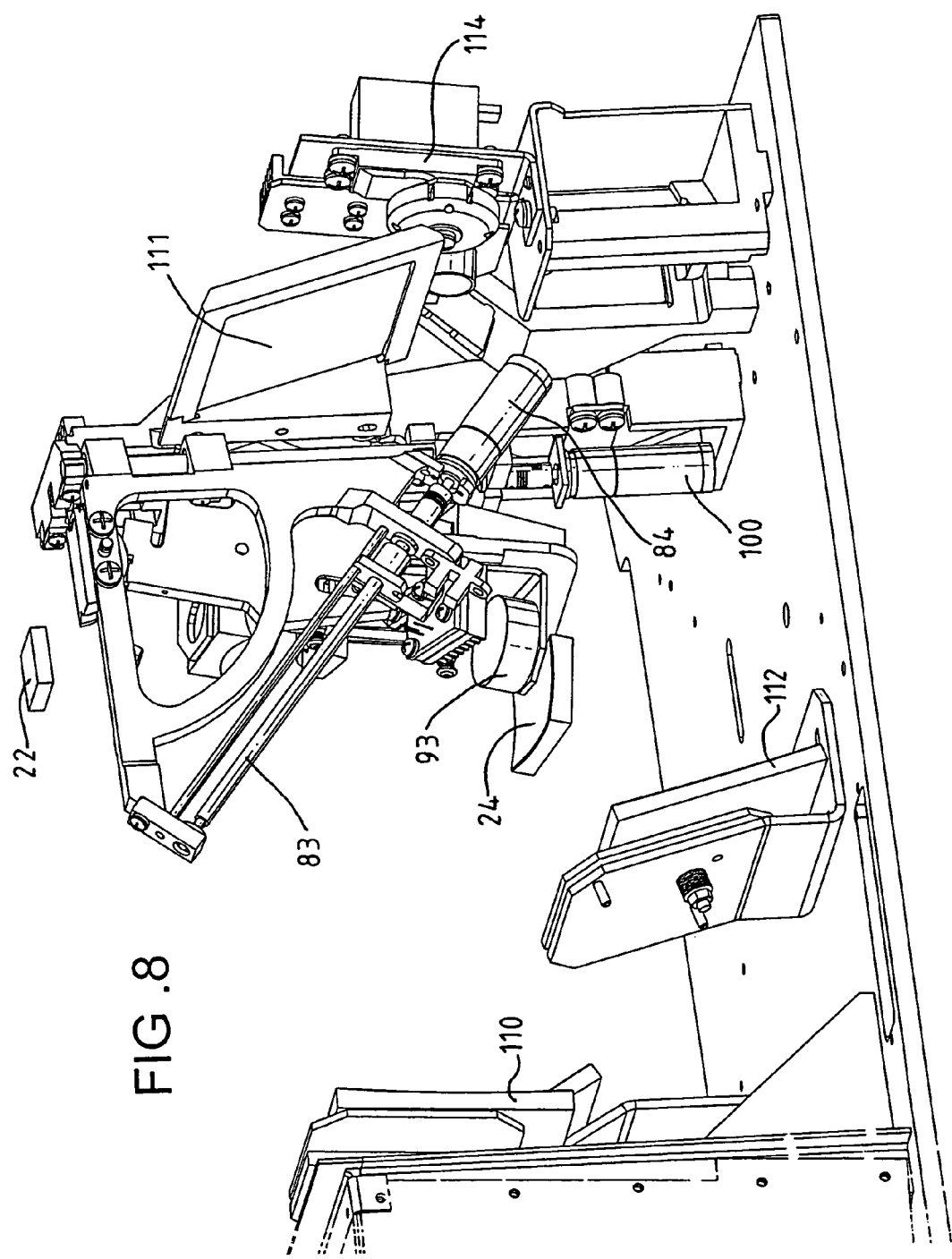
FIG. 8 is a partial view from the rear right of the reflectance accessory.
Figure 9:
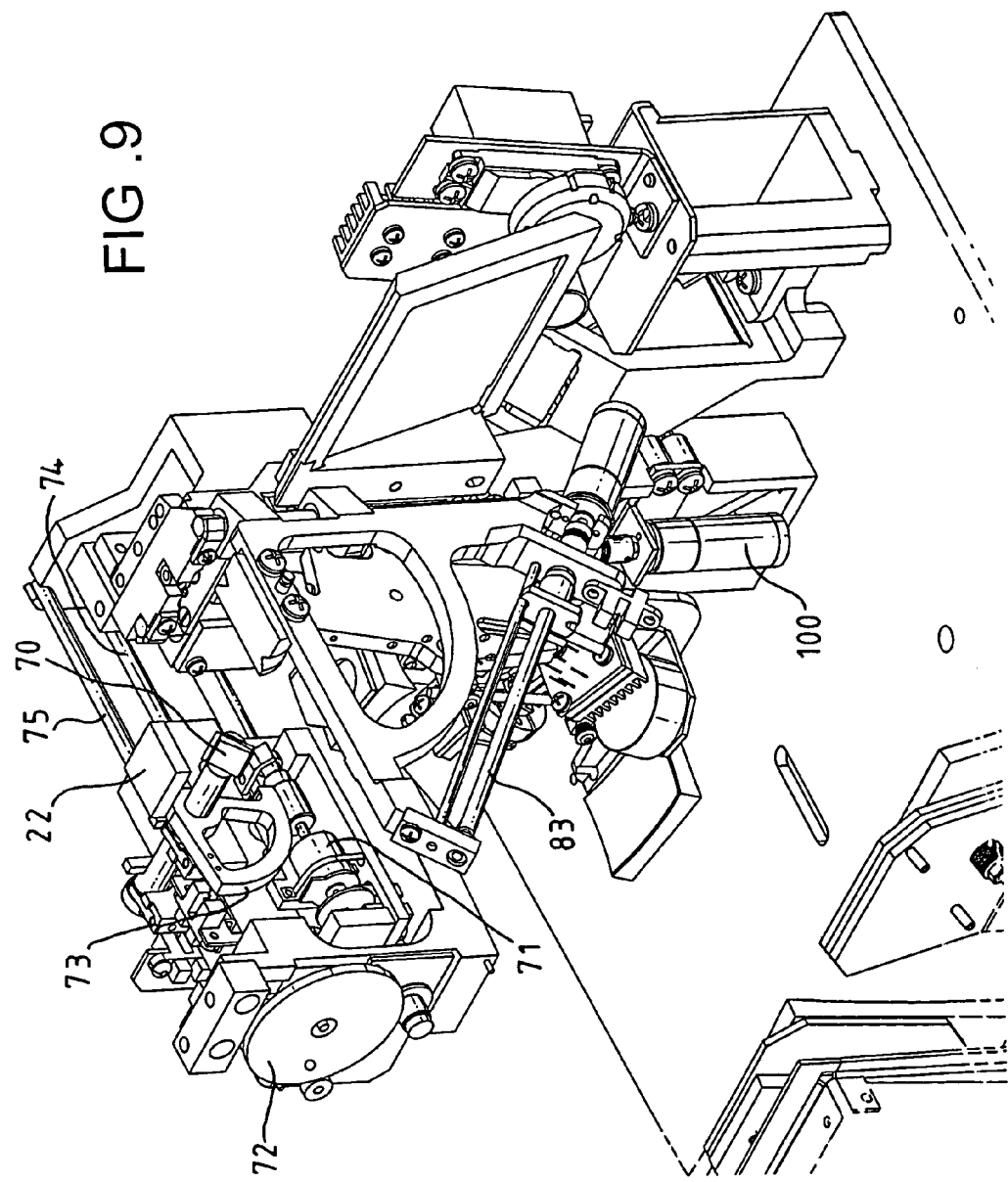
FIG. 9 is a view from the rear right showing the steering mirror and detector assembly.
Figure 10:
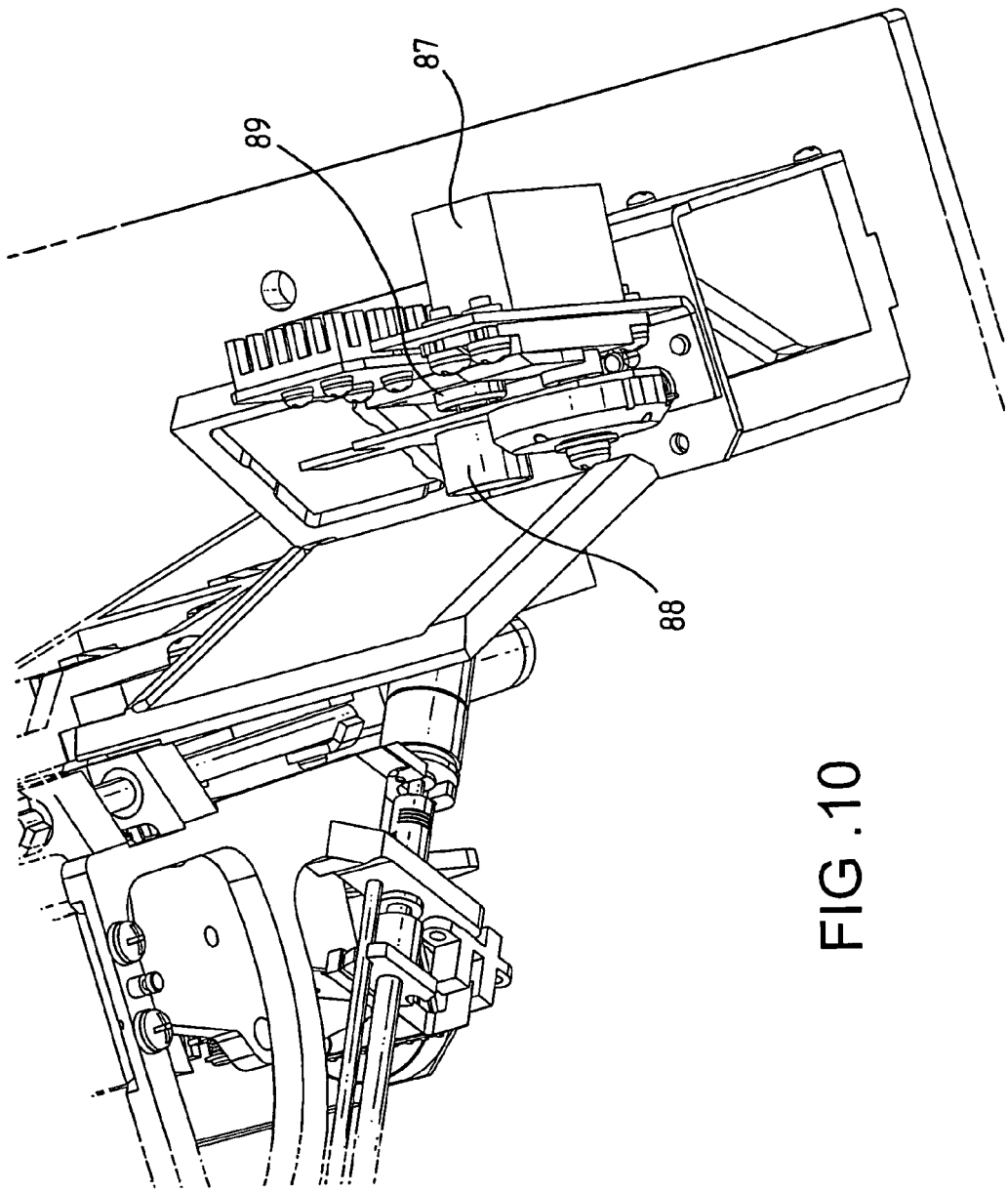
FIG. 10 is a view from the rear showing the detector assembly.

In FIG. 3 the steering mirror assembly is shown at (20) and the sample location is shown at (22). The collector mirror is shown at (24) and the detector assembly at (26). The steering mirror assembly as shown in FIGS. 3 and 9 comprises a pivotally mounted mirror (70) with a drive assembly including a motor (76), a lead screw transmission (72), a worm drive motor (71) (only shown in FIG. 9), a worm wheel sector (73), lead screw (74) and a slide (75). The motor (76) seen at the centre of FIG. 3 can be energised to rotate the lead screw (74) and cause linear translational movement of the mirror (70) guided by the slide (75). The worm drive motor (71) (only shown in FIG. 9) can be used to rotate the plane of the mirror (70).

The detector assembly is shown in more detail in FIGS. 4, 6, 7, 8 and 9. The detector assembly includes a bracket (80) which is mounted so that it is movable along an arc defined by a curved member (81) and a hub (120). This arc is centred in the lateral and vertical dimensions on the sample location (22). The curved member (81) is supported by an arm (82) which supports one end of a lead screw (83), which can be driven by a motor (84). When the motor (84) is energised the lead screw rotates and causes the bracket (80) to move along an arcuate path corresponding to the arc defined by the arcuate element (81) about the sample location as pivot point.

Figure 11:
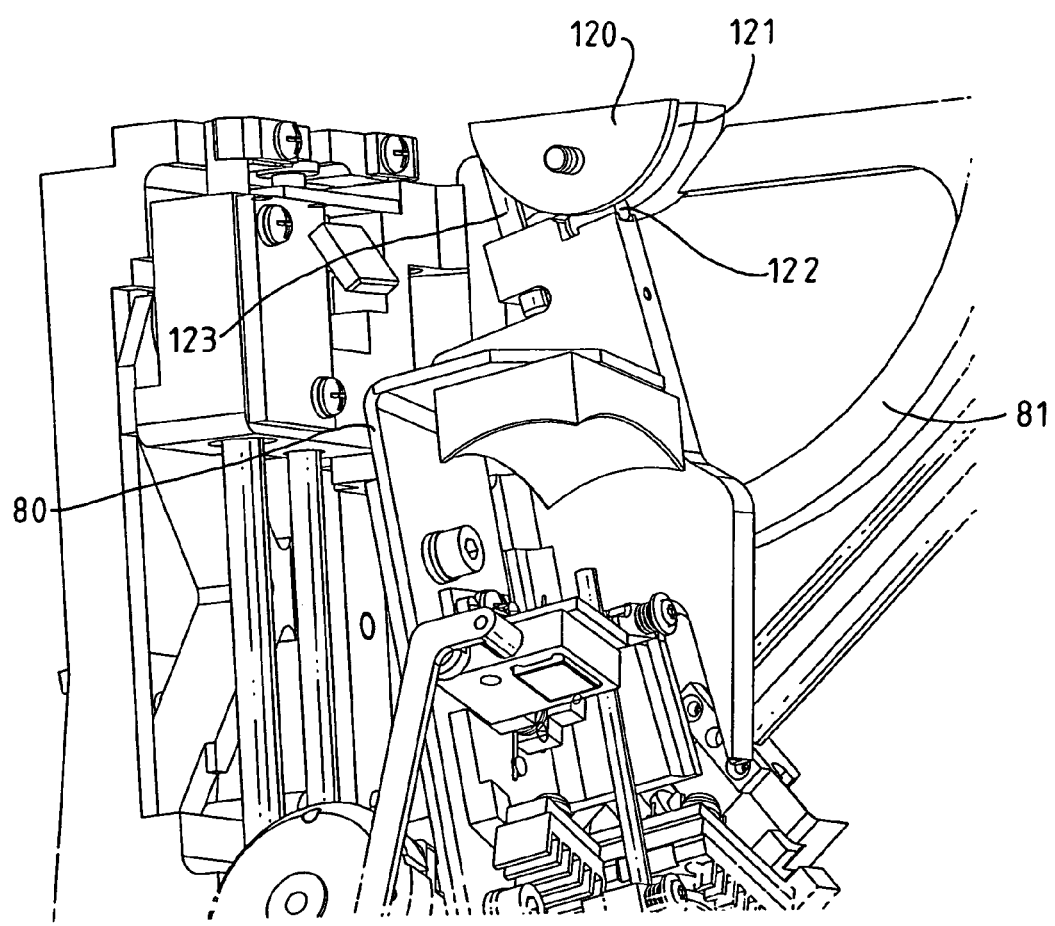
FIG. 11 is a view from low front right showing a mechanism for controlling arcuate movement of the detector assembly.
Figure 12:
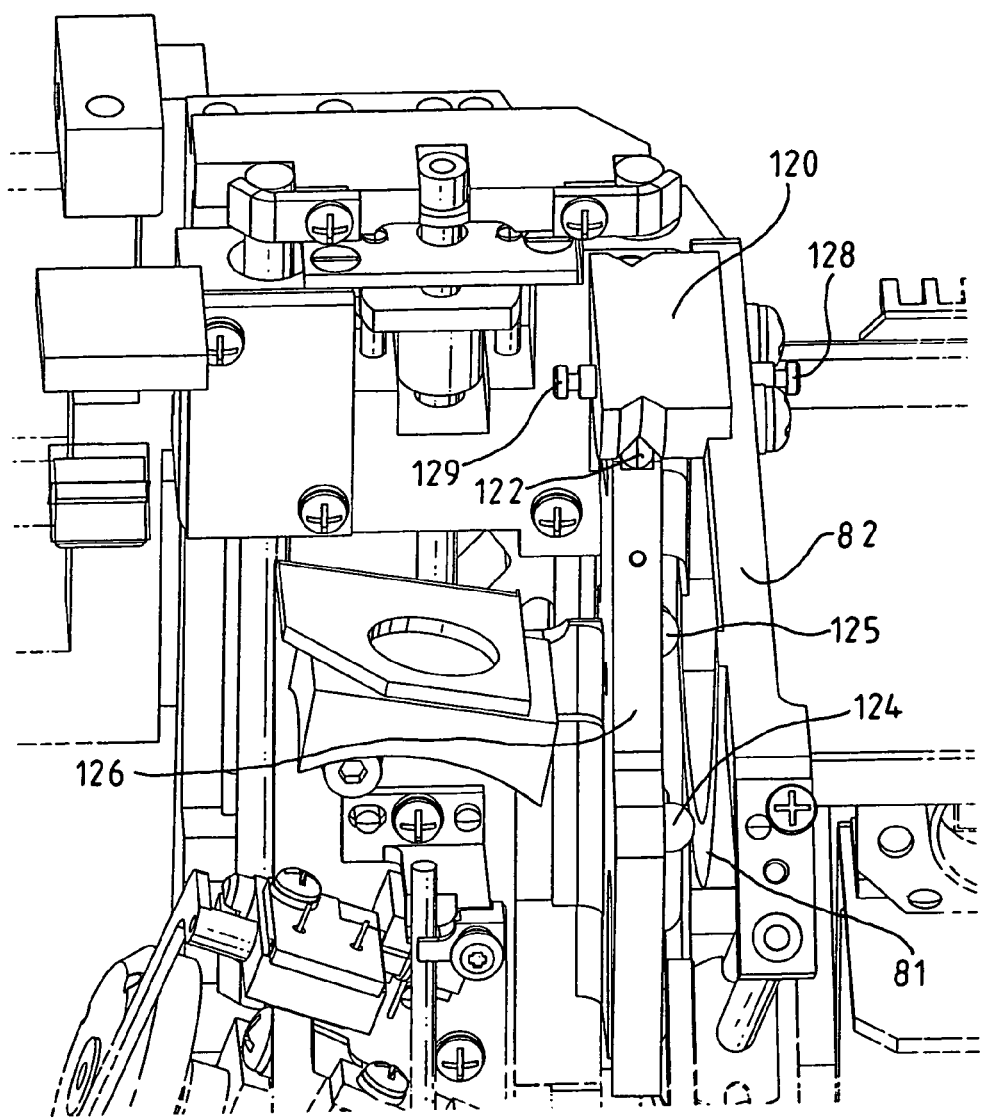
FIG. 12 is a view partly from above showing the mechanism of FIG. 11.

FIGS. 11 and 12 show the mechanism for controlling arcuate movement of the detector assembly. The mechanism includes the hub (120) mounted alongside the arm (82). The hub (120) has an arcuate groove (121) in which are located two pins (122, 123). The pins (122 and 123) are disposed with their axes generally at right angles to each other. The pin (123) is fixed to a detector sub-plate (124) and the pin (122) rests freely on an end surface of the sub-plate. Two balls (124, 125) are carried by the detector sub-plate (126) and are arranged so that they can run along an arcuate track defined by the arcuate element (81).

In use the detector assembly is constrained to move in an arc by the two pins (122, 123) running in the groove (121) and by the two balls (124,125) running on the arcuate track. The plane of the arcuate motion is defined by the two balls and the larger (123) of the two pins which is fixed to the sub-plate (126). These elements define a three point mounting. The other pin (122) is free to float perpendicular to this plane, but constrains the rotation to be about the centre of rotation of the arc of the groove (121).

Contact of the bearing surfaces is maintained by spring pressure from extension springs (not shown) which join spring posts (128,129) to the detector sub-plate (126). The centre of rotation lies in the plane of the sample.

To permit samples of arbitrary size to be placed on the top plate (51) the accessory is designed so that no components extend above the plane of the top-plate (51) and this precludes the use of a conventional axle for the arc rotation. To achieve the required design the cross-section of the hub (120) is machined to be slightly less than a semi-circle.

The bracket (80) supports a number of elements which form part of the detector assembly. There are two detector elements, one of these being a silicon detector (88) and the other being a lead suiphide detector (89). The silicon detector (88) is mounted so that it can be moved into or out of the path of radiation reflected by the collector mirror (24). A motor (87) is provided and can be energised to cause the detector to be moved. When the detector (88) is in the path of the beam reflected by the mirror (24) radiation does not reach the lead suiphide detector (89).

A lightpipe (90) is associated with the lead sulphide detector (89) and arranged so that when the silicon detector is not in an operative position radiation reflected by the collector (24) is directed to a lightpipe input mirror (92) and then is reflected along a path extending through the lightpipe (90) and onto the lead sulphide detector (89).

The reason for providing two detectors (88 and 89) is to enable the accessory to operate at different wavelengths. The silicon diode detector (88) is provided for relatively short wave detection. Such detectors have excellent uniformity and for reasons discussed earlier can be used without any optical scrambling. The lead sulphide detector (89) is provided for detection at longer wavelengths, but these detectors have a problem in that their response can be quite non-uniform over the surface area of the detector. This means that it is necessary to use an optical scrambler in order to counteract the effects of such non-uniformities. In the present embodiment the light pipe (90) acts as an optical scrambler and it has been found to be particularly suitable in this application. Typically the dimensions of the pipe are a length of 50 mm and a diameter of 3 mm. The lightpipe comprises a glass rod with smooth sides polished at both ends and selected to have good transmission over the full spectral range. A particularly suitable glass is Suprasil 300, which has excellent transmission to beyond 2500 nm. In use an image of the sample is formed by the concave lightpipe input mirror (92) onto the input end of the lightpipe (90). Multiple internal reflections in the lightpipe then scramble the image to produce a substantially uniform patch of light at the output end of the lightpipe. This light is then refocussed onto the lead sulphide detector (89) by a lightpipe output mirror (93). It is important to ensure that the sample image underfills the lightpipe input to ensure that small movements of the image do not lead to radiation missing in the lightpipe. The scrambling ensures that distribution of light emerging from the lightpipe remains substantially unchanged so that even if the detector is inhomogeneous the output signal is unchanged either for small image movements or for image inversion.

The assembly of components mounted on bracket (80) is also movable linearly relative to the sample position for reasons explained earlier and this is achieved by means of a motor (100). The motor (100) can be energised to rotate a lead screw (101) and this causes the detector assembly to move upwardly or downwardly, the movement being guided by a slide (102).

The accessory has an electronics unit (104) which can be coupled to the processing circuitry of the spectrometer and is used to provide signals for energising the motors in order to correctly position of the moveable components for the particular reflectance measurement being carried out.

Figure 13:
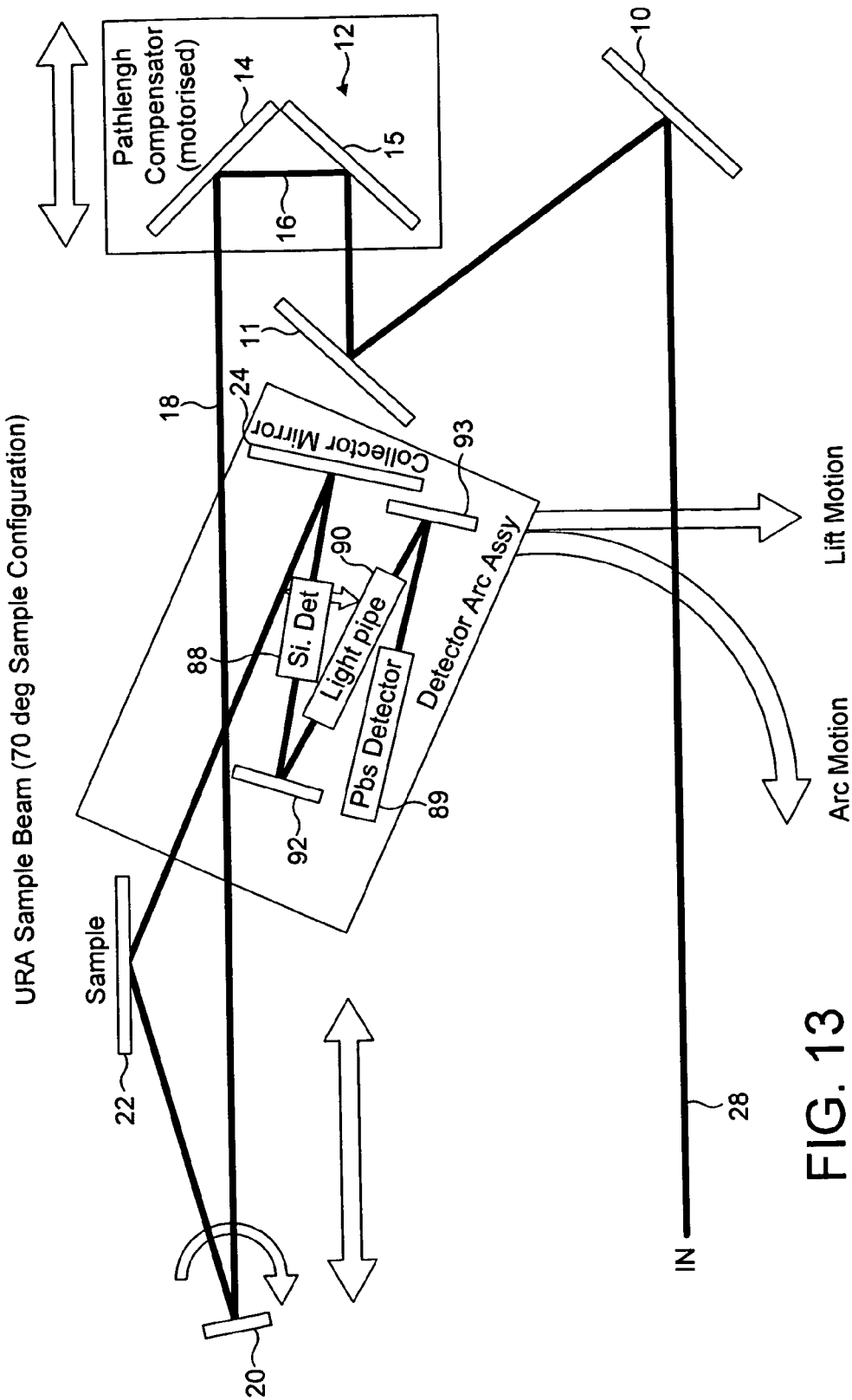
FIGS. 13 to 16 are schematic views illustrating how the components of the accessory move in different measurement configurations.
Figure 14:
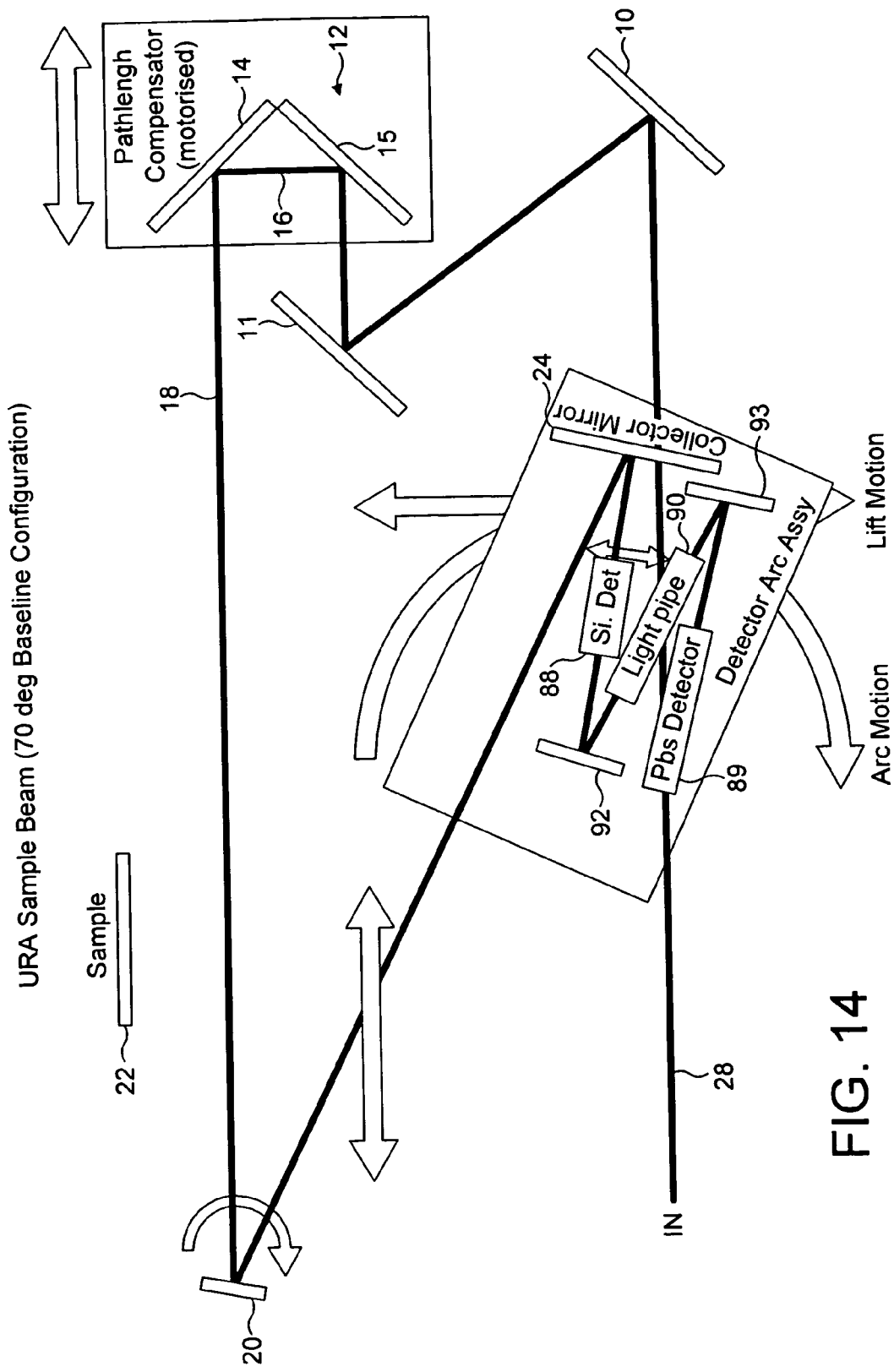

The relative positions of the components of the accessory for various measurements is illustrated in FIGS. 13, 14, 15 and 16. FIG. 13 illustrates the relative position of the components of the accessory when a reflectivity measurement is carried out on a sample mounted at the sample location (22) and the beam is incident on the sample at an angle of 70 degrees. It should be noted that in FIGS. 13 to 16, the path length compensator (12) is shown rotated through 90 degrees to its actual configuration in order to illustrate the path of the beam. FIG. 14 shows the position of the components for carrying out what is known as a baseline measurement corresponding to the 70 degree measurement. In this configuration the beam does not reflect from the sample. As will be appreciated by those skilled in the art it is necessary to carry out a measurement under conditions in which the beams does not reflect from the sample and compare that with the results obtained when the beam does reflect off the sample as shown in FIG. 11.

Figure 15:
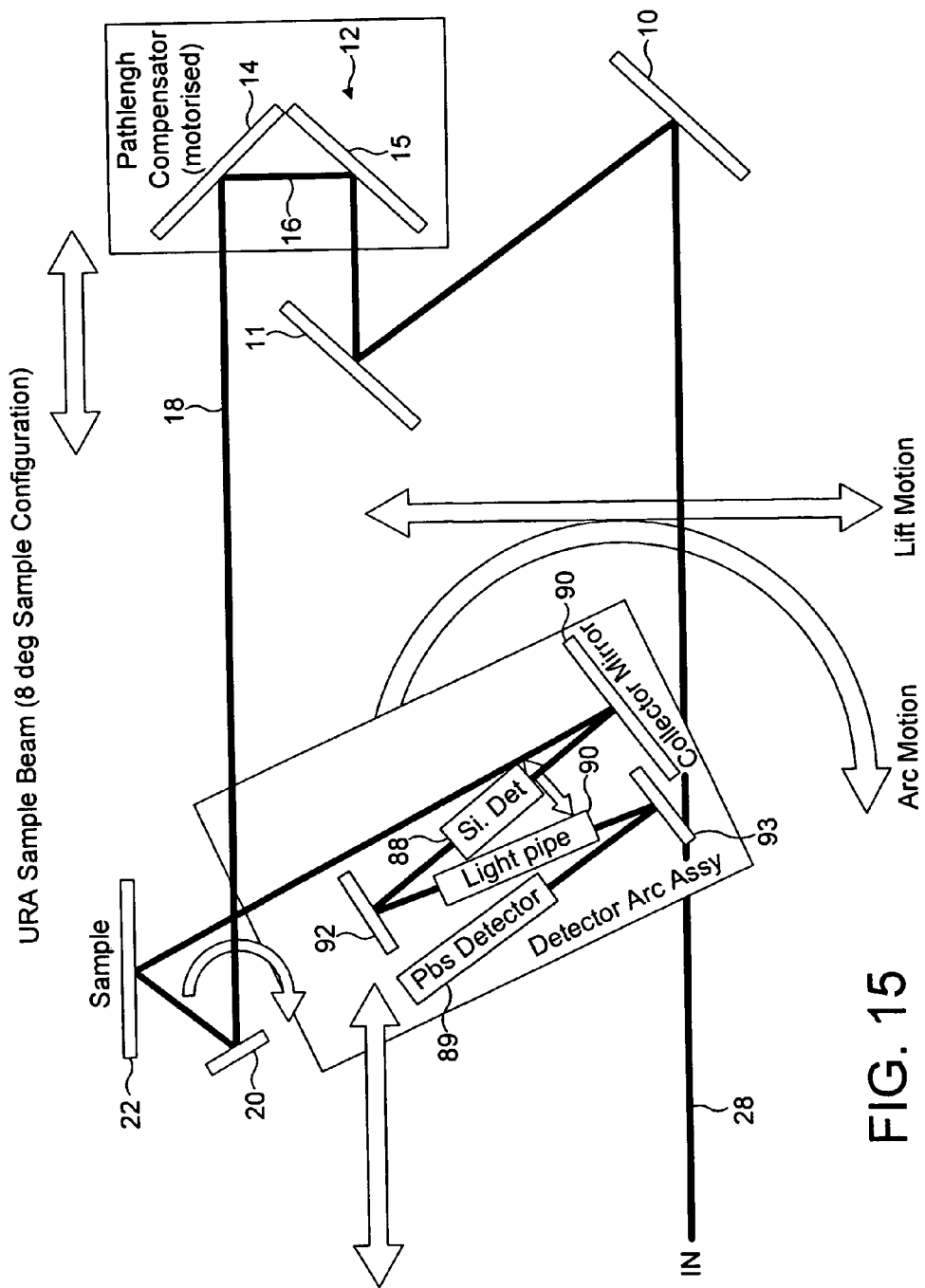
Figure 16:
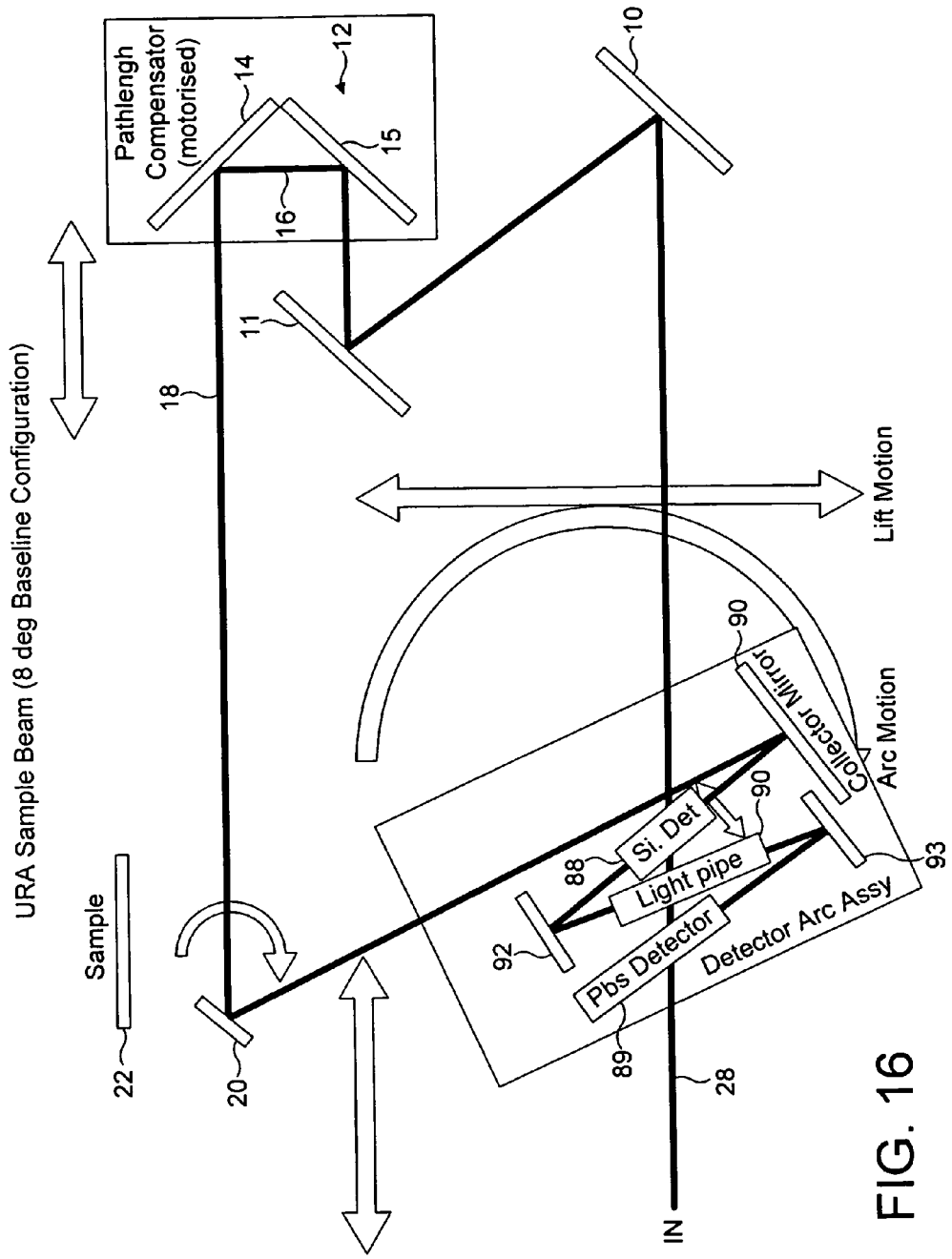

FIGS. 15 and 16 are views corresponding to those of FIGS. 13 and 14, but illustrate the situation where the components have been adjusted to a position in which the radiation is incident on the sample at an angle of 8 degrees.

8 Degrees and 70 degrees represent the end points of the range of angles over which the accessory can be used to measure reflectance of a sample. It will be appreciated that by appropriate movement of the movable components of the accessory a measurement of the reflectance of a sample can be carried out at any angle in the range 8 degrees to 70 degrees.

As will be appreciated by those skilled in the art the spectrometer produces a reference beam as well as a sample beam. The accessory includes reference beam mirrors (110, 111, and 112) and a reference beam detector (114) (see FIG. 8), but a detailed description of these elements is not given as it is not necessary for an understanding of the present invention.

A particularly significant feature of the design of accessory described above is that all the components of the accessory are disposed below the horizontal surface of the top plate (51).

What is claimed is:

1. An accessory for use with a spectrometer to enable reflectance measurements to be made on a sample, said accessory comprising:
    a housing defining a sample location,
    a first reflector for receiving analyzing radiation propagating generally horizontally and for reflecting the radiation at least partially upwardly to a second reflector,
    a third reflector for receiving radiation from the second reflector and for directing the radiation along a generally horizontal path which is horizontally displaced relative to that of the incoming radiation,
    a fourth reflector for directing the radiation towards the sample location, said fourth reflector being rotatable and translatable by at least one first motor, and
    a detector located in said housing for receiving radiation reflected from the sample, wherein the detector is movable along an arc and linearly translatable by at least one second motor; and
    wherein said at least one first motor and said at least one second motor can position said fourth reflector and said detector such that the radiation is incident on the sample at a number of different angles of incidence and also to provide a configuration in which the radiation is directed to the detector without being incident on the sample.

2. An accessory according to claim 1, wherein the direction of radiation propagating from the third reflector is generally opposite to that of the incoming radiation.

3. An accessory according to claim 1, wherein the third reflector is a roof mirror.

4. An accessory according to claim 3, wherein the third reflector is movable linearly so that it can act as a path length compensator.

* * * * *

UNITED STATES PATENT AND TRADEMARK OFFICE
CERTIFICATE OF CORRECTION

PATENT NO. : 7,595,884 B2  Page 1 of 1
APPLICATION NO. : 11/040535
DATED : September 29, 2009
INVENTOR(S) : Robert Alan Hoult et al.

It is certified that error appears in the above-identified patent and that said Letters Patent is hereby corrected as shown below:

Title page,

Item (30) Foreign Application Priority Data should read:
-- January 20, 2004   (EP)............................... 04250265 --

Signed and Sealed this

Twenty-fourth Day of November, 2009

David J. Kappos
*Director of the United States Patent and Trademark Office*